United States Patent
Zones et al.

(10) Patent No.: US 10,160,657 B2
(45) Date of Patent: Dec. 25, 2018

(54) HIGH-SILICA SSZ-32X ZEOLITE

(71) Applicant: Chevron U.S.A. Inc., San Ramon, CA (US)

(72) Inventors: Stacey Ian Zones, San Francisco, CA (US); Cong-Yan Chen, Kensington, CA (US); Adeola Florence Ojo, Pleasant Hill, CA (US)

(73) Assignee: Chevron U.S.A. Inc., San Ramon, CA (US)

(*) Notice: Subject to any disclaimer, the term of this patent is extended or adjusted under 35 U.S.C. 154(b) by 0 days.

(21) Appl. No.: 15/785,504

(22) Filed: Oct. 17, 2017

(65) Prior Publication Data

US 2018/0134572 A1    May 17, 2018

Related U.S. Application Data

(60) Provisional application No. 62/423,259, filed on Nov. 17, 2016.

(51) Int. Cl.
| | | |
|---|---|---|
| *C01B 39/48* | (2006.01) | |
| *B01J 29/74* | (2006.01) | |
| *B01J 29/70* | (2006.01) | |
| *C07C 5/27* | (2006.01) | |
| *C01B 39/02* | (2006.01) | |

(52) U.S. Cl.
CPC .......... *C01B 39/48* (2013.01); *B01J 29/7046* (2013.01); *B01J 29/74* (2013.01); *C01B 39/026* (2013.01); *C07C 5/2775* (2013.01); *C01P 2004/64* (2013.01); *C07C 2529/74* (2013.01)

(58) Field of Classification Search
CPC .... C01B 39/48; C01B 39/026; B01J 29/7046; C01P 2004/64
See application file for complete search history.

(56) References Cited

U.S. PATENT DOCUMENTS

| | | | |
|---|---|---|---|
| 5,053,373 A | 10/1991 | Zones | |
| 5,252,527 A | 10/1993 | Zones | |
| 7,157,075 B1* | 1/2007 | Burton, Jr. | C01B 39/48 |
| | | | 423/705 |
| 7,390,763 B2 | 6/2008 | Zones et al. | |
| 7,468,126 B2 | 12/2008 | Zones et al. | |
| 7,569,507 B2 | 8/2009 | Zones et al. | |
| 8,545,805 B2 | 10/2013 | Zones et al. | |
| 2004/0052726 A1* | 3/2004 | Davis | C01B 37/00 |
| | | | 423/700 |

FOREIGN PATENT DOCUMENTS

| | | | |
|---|---|---|---|
| CN | 105645428 A | * | 6/2016 |
| EP | 0347273 A1 | | 12/1989 |
| WO | 9629284 A1 | | 9/1996 |
| WO | WO1996029286 | * | 9/1996 |

OTHER PUBLICATIONS

Liu et al.,"SAynthesis of ZSM-23 Zeolite using isopropylamine as template", Chinese Journal of Caralysis, vol. 30, iss. 6, pp. 525-530 (Jun. 2009) (Year: 2009).*
PCT International Search Report, International Patent Appl. No. PCT/US2017/056936, dated Jan. 2, 2018.

* cited by examiner

Primary Examiner — David M Brunsman
(74) *Attorney, Agent, or Firm* — Terrence Flaherty

(57) ABSTRACT

The present disclosure is directed to a high-silica form of zeolite SSZ-32x, its synthesis in fluoride media using dipropylamine as a structure directing agent, and its use in catalytic processes.

11 Claims, 3 Drawing Sheets

HIGH-SILICA SSZ-32X ZEOLITE

CROSS REFERENCE TO RELATED APPLICATIONS

This application claims priority to U.S. Provisional Application Ser. No. 62/423,259, filed on Nov. 17, 2016, the disclosure of which is fully incorporated herein by reference.

TECHNICAL FIELD

This disclosure relates generally to a high-silica form of zeolite SSZ-32x, its synthesis, and its use in catalytic processes.

BACKGROUND

Molecular sieves are a commercially important class of crystalline materials. They have distinct crystal structures with ordered pore structures which are demonstrated by distinct X-ray diffraction patterns. The crystal structure defines cavities and pores which are characteristic of the different species. Molecular sieves such as zeolites have been used extensively in catalysis, adsorption, separation, and chromatography.

Molecular sieves are classified by the Structure Commission of the International Zeolite Association according to the rules of the IUPAC Commission on Zeolite Nomenclature. According to this classification, framework type zeolites and other crystalline microporous molecular sieves, for which a structure has been established, are assigned a three-letter code and are described in the "*Atlas of Zeolite Framework Types*" Sixth Revised Edition, Elsevier (2007).

Molecular sieves having a MTT-type framework code have a one-dimensional 10-ring pore system. MTT-type molecular sieves have very similar, but not identical, X-ray diffraction patterns. SSZ-32 and its small crystal variant, SSZ-32x, are known MTT-type molecular sieves.

SSZ-32 and methods for making it in the presence of N-lower alkyl-N'-isopropylimidazolium cations are disclosed in U.S. Pat. Nos. 5,053,373 and 5,252,527. SSZ-32 is reported to have a $SiO_2/Al_2O_3$ molar ratio in a range of 20 to less than 40.

SSZ-32x and methods for making it in the presence of N-lower alkyl-N'-isopropylimidazolium cations are disclosed in U.S. Pat. Nos. 7,390,763 and 8,545,805. SSZ-32x is reported to have a $SiO_2/Al_2O_3$ molar ratio in a range of 20 to less than 40 with crystallites having small broad lathe-like components in a range of 20 to 40 nm.

SSZ-32x, in comparison with standard SSZ-32, has broadened X-ray diffraction peaks that may be a result of its inherent small crystals, altered argon adsorption ratios, increased external surface area and reduced cracking activity over other intermediate pore size molecular sieves used for a variety of catalytic processes.

According to the present disclosure, it has now been found that dipropylamine is effective as a structure directing agent in the synthesis of high-silica forms of SSZ-32x in fluoride media.

SUMMARY

In one aspect, there is provided a method for synthesizing zeolite SSZ-32x comprising: (a) preparing a reaction mixture comprising: (1) a source of silicon oxide; (2) a source of aluminum oxide; (3) dipropylamine; (4) a source of fluoride ions; and (5) water; and (b) subjecting the reaction mixture to crystallization conditions sufficient to form crystals of the zeolite.

In another aspect, there is provided a SSZ-32x zeolite having a $SiO_2/Al_2O_3$ molar ratio of at least 50.

In yet another aspect, there is provided a SSZ-32x zeolite comprising dipropylamine in its pores.

In a further aspect, there is provided a process for converting a feedstock comprising an organic compound to a conversion product which comprises contacting the feedstock at organic compound conversion conditions with a catalyst comprising an active form of the SSZ-32x zeolite described herein.

BRIEF DESCRIPTION OF THE DRAWINGS

FIG. 2(a) is a plot of n-decane conversion as a function of temperature. FIG. 2(b) is a plot of product distribution as a function of conversion.

FIG. 3(a) is a plot of n-decane conversion as a function of temperature. FIG. 3(b) is a plot of product distribution as a function of conversion.

DETAILED DESCRIPTION

Introduction

Figure 1:
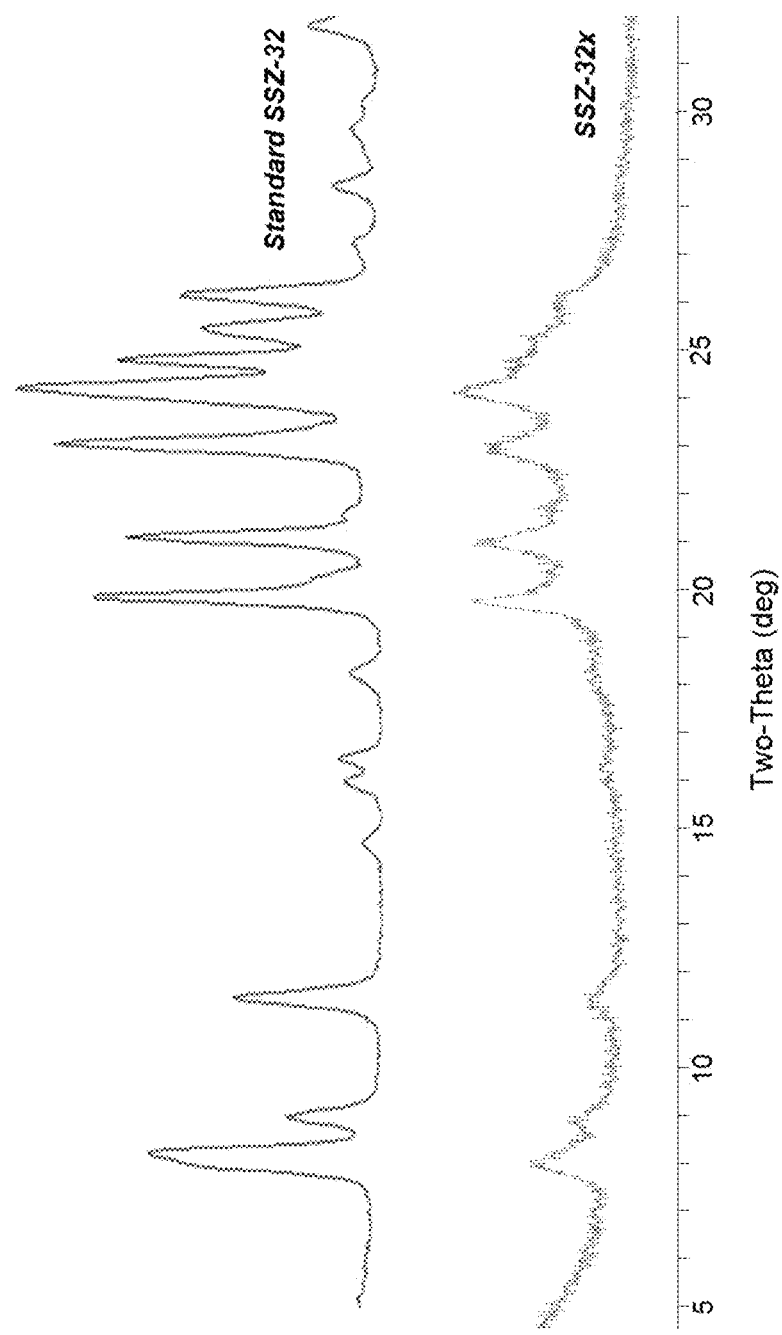
FIG. 1 compares the powder X-ray diffraction (XRD) patterns of conventional (standard) SSZ-32 zeolite (top pattern) and SSZ-32x zeolite prepared according to Example 1 (bottom pattern).

The following terms will be used throughout the specification and will have the following meanings unless otherwise indicated.

The term "zeolite" refers to crystalline aluminosilicate compositions which are microporous and which are formed from corner-sharing $AlO_2$ and $SiO_2$ tetrahedra.

The term "SSZ-32x" refers herein to a zeolite of the structure of SSZ-32 and characterized as having crystallite sizes of less than 100 nm.

The term "crystallite size" refers to the longest dimension of a crystal. The crystallite size can be determined by XRD analysis using procedures and equipment available in the art.

The term "as-synthesized" refers to a zeolite in its form after crystallization, prior to removal of the structure directing agent.

The term "anhydrous" is employed herein to refer to a zeolite substantially devoid of both physically adsorbed and chemically adsorbed water.

The term "colloid" and other like terms including "colloidal," "sol," and the like refer to a two-phase system having a dispersed phase and a continuous phase. The colloids of the present disclosure have a solid phase dispersed or suspended in a continuous or substantially continuous liquid phase, typically an aqueous solution. Colloids are stable mixtures and the dispersed phase generally does not settle out of the mixture.

The term "standard cubic feet per barrel" is abbreviated as "scf/B".

As used herein, the numbering scheme for the Periodic Table Groups is as disclosed in *Chem. Eng. News,* 63(5), 26-27 (1985).

Reaction Mixture

In general, SSZ-32x zeolite is prepared by: (a) preparing a reaction mixture comprising (1) a source of silicon oxide; (2) a source of aluminum oxide; (3) dipropylamine (Q); (4) a source of fluoride ions; and (5) water; and (b) subjecting the reaction mixture to crystallization conditions sufficient to form crystals of the zeolite.

The composition of the reaction mixture from which the zeolite is formed, in terms of molar ratios, is identified in Table 1 below:

TABLE 1

| Reactants | Broad | Exemplary |
|---|---|---|
| $SiO_2/Al_2O_3$ | ≥50 | 50 to 500 |
| $Q/SiO_2$ | 0.10 to 0.60 | 0.10 to 0.60 |
| $F/SiO_2$ | 0.10 to 0.60 | 0.10 to 0.60 |
| $H_2O/SiO_2$ | 10 to 60 | 15 to 40 | wherein compositional variable Q represents dipropylamine.

Suitable sources of silicon oxide include colloidal silica, fumed silica, precipitated silica, alkali metal silicates, and tetra-alkyl orthosilicates.

Suitable sources of aluminum oxide include hydrated alumina and water-soluble aluminum salts (e.g., aluminum nitrate).

Combined sources of silicon oxide and aluminum oxide can additionally or alternatively be used and can include aluminosilicate zeolites (e.g., zeolite Y), colloidal aluminosilicates, and clays or treated clays (e.g., metakaolin).

Suitable sources of fluoride ions include hydrogen fluoride, ammonium fluoride, and ammonium hydrogen difluoride.

The reaction mixture may also contain seeds of a molecular sieve material, such as SSZ-32x from a previous synthesis, desirably in an amount from 0.01 to 10,000 ppm (e.g., 100 ppm to 5,000 ppm) by weight of the reaction mixture.

For each embodiment described herein, the reaction mixture may be supplied by more than one source. Also, two or more reaction components may be provided by one source.

The reaction mixture may be prepared either batch wise or continuously. Crystal size, morphology and crystallization time of the crystalline zeolite described herein may vary with the nature of the reaction mixture and the crystallization conditions.

Crystallization and Post-Synthesis Treatment

Crystallization of the zeolite from the above reaction mixture can be carried out under either static, tumbled or stirred conditions in a suitable reactor vessel, such as for example polypropylene jars or Teflon-lined or stainless steel autoclaves, at a temperature of from 125° C. to 200° C. for a time sufficient for crystallization to occur at the temperature used, e.g., from 3 to 15 days. Crystallization is usually carried out in a closed system under autogenous pressure.

Once the zeolite crystals have formed, the solid product is recovered from the reaction mixture by standard mechanical separation techniques such as centrifugation or filtration. The crystals are water-washed and then dried to obtain the as-synthesized zeolite crystals. The drying step is typically performed at a temperature of less than 200° C.

As a result of the crystallization process, the recovered crystalline zeolite product contains within its pore structure at least a portion of the structure directing agent used in the synthesis.

The as-synthesized zeolite product may also be subjected to treatment to remove part or all of the organic structure directing agent used in its synthesis. This can be conveniently accomplished by thermal treatment, in which the as-synthesized material can be heated to a temperature of at least 370° C. for at least 1 minute and generally not longer than 20 hours. The thermal treatment can be performed at a temperature up to 925° C. While sub-atmospheric pressure can be employed for the thermal treatment, atmospheric pressure can be desired for reasons of convenience. Additionally or alternatively, the organic structure directing agent can be removed by treatment with ozone (see, e.g., A. N. Parikh et al., *Micropor. Mesopor. Mater.* 2004, 76, 17-22). The organic-free product, especially in its metal, hydrogen and ammonium forms, is particularly useful in the catalysis of certain organic (e.g., hydrocarbon) conversion reactions. In the present disclosure, the organic-free molecular sieve in its hydrogen form is referred to as "active form" of the molecular sieve, with or without metal function present.

The present zeolite synthesis can be carried out in the absence of Group 1 and/or Group 2 metal cations, thereby obviating the need for ion-exchange of the product after thermal treatment to remove any occluded structure directing agent. Any cations in the as-synthesized zeolite can be replaced in accordance with techniques well known in the art, e.g., by ion exchange with other cations. Preferred replacing cations can include metal ions, hydrogen ions, hydrogen precursor (e.g., ammonium) ions, and combinations thereof. Particularly preferred replacing cations can include those that can tailor the catalytic activity for certain organic compound conversion reactions. Such cations include hydrogen, rare earth metals, and/or one or more metals of Groups 2-15 of the Periodic Table of the Elements.

The present zeolite may be intimately combined with a hydrogenating component, such as chromium, molybdenum, manganese, rhenium, cobalt, nickel, and/or a noble metal such as palladium or platinum, where a hydrogenation-dehydrogenation function may be performed. Such component can be in the composition by way of co-crystallization, exchanged into the composition, impregnated therein, intimately physically admixed therewith, or via any suitable method known to those in the art.

When used as a catalyst, it may be desirable to incorporate the present zeolite with another material that is resistant to the temperatures and other conditions employed in organic conversion processes. Such materials include active and inactive materials and synthetic or naturally occurring zeolites as well as inorganic materials such as clays, silica and/or metal oxides such as alumina. The latter may be either naturally occurring or in the form of gelatinous precipitates or gels, including mixtures of silica and metal oxides. Use of a material in conjunction with the present zeolite, i.e., combined therewith or present during synthesis of the zeolite, which is active, tends to change the conversion and/or selectivity of the catalyst in certain organic conversion processes.

Moreover, inactive materials suitably serve as diluents to control the amount of conversion in a given process so that products can be obtained in an economic and orderly manner without employing other means for controlling the rate of reaction. Such inactive materials may be incorporated into naturally occurring clays, e.g., bentonite and kaolin, to improve the crush strength of the catalyst under commercial operating conditions. These materials (i.e., clays, oxides, etc.) function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the present zeolite include the montmorillonite and kaolin family, which families include the sub-bentonites, and the kaolins commonly known as Dixie, McNamee, Ga. and Florida clays or others in which the main mineral constituent is halloysite, kaolinite, dickite, nacrite, or anauxite. Such clays can be used in the raw state as originally mined or initially subjected to calcination, acid treatment or chemical modification.

Binders useful for compositing with the present zeolite also include inorganic oxides, such as silica, zirconia, titania, magnesia, beryllia, alumina, and mixtures thereof.

In addition to the foregoing materials, the present zeolite can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of SSZ-32x zeolite and matrix may vary widely, with the SSZ-32x content ranging from 1 to 90% by weight (e.g., 2 to 80% by weight) of the composite.

Characterization of the Zeolite

In its as-synthesized and anhydrous form, the present SSZ-32x zeolite has a chemical composition, in terms of molar ratios, as described in Table 2 below.

TABLE 2

| | Broad | Exemplary |
|---|---|---|
| $SiO_2/Al_2O_3$ | ≥50 | 50 to 500 |
| $Q/SiO_2$ | >0 to 0.1 | >0 to 0.1 |
| $F/SiO_2$ | >0 to 0.1 | >0 to 0.1 | wherein Q represents dipropylamine. In contrast, standard SSZ-32 and previously reported forms of SSZ-32x have a $SiO_2/Al_2O_3$ molar ratio in a range of 20 to less than 40.

It should be noted that the as-synthesized form of the present zeolite may have mole ratios different from the mole ratios of reactants of the reaction mixture used to prepare the as-synthesized form. This result may occur due to incomplete incorporation of 100% of the reactants of the reaction mixture into the crystals formed (from the reaction mixture).

Generally, the present SSZ-32x zeolite is in the form of aggregates of small crystals having crystallite sizes of less than 100 nm (e.g., 15 to 60 nm, or 20 to 40 nm). In contrast, standard SSZ-32 crystals are elongated having crystallite sizes of greater than 100 nm (e.g., about 150 to 200 nm).

In some aspects, the present SSZ-32x zeolite may have one or more of the following additional properties: an argon adsorption ratio (ArAR) of greater than 0.5 (e.g., 0.55 to 0.70) and an external surface area of at least 80 m²/g (e.g., 80 to 300 m²/g or 100 to 250 m²/g).

The argon adsorption ratio (ArAR) is calculated as follows:

$$ArAR = \frac{\text{Ar adsorption at 87K between the relative pressures of 0.001 and 0.1}}{\text{total Ar adsorption up to relative pressure of 0.1}}$$

Standard SSZ-32 has an argon adsorption ratio of less than 0.5 (e.g., 0.35-0.45).

External surface area is determined by argon physisorption. Standard SSZ-32 has an external surface area of about 50 m²/g. Argon physisorption experiments can be performed by methods known in the art (see, e.g., C-Y. Chen et al., Chem. Eur. J. 1998, 4, 1312-1323).

In its calcined form, the present zeolite has a chemical composition comprising the molar relationship:

$Al_2O_3$:(n)$SiO_2$ wherein n≥50 (e.g., 50 to 500, 50 to 300, 50 to 200, 50 to 100, 50 to 75, 60 to 500, 60 to 300, 60 to 200, 60 to 100, or 60 to 75).

As taught by U.S. Pat. No. 5,053,373, zeolite SSZ-32 ("standard SSZ-32") has an X-ray diffraction including the characteristic lines listed in Table 3 below.

TABLE 3

| d-spacing, nm | Relative Intensity[a] |
|---|---|
| 1.105 | M |
| 1.005 | W |
| 0.783 | W |
| 0.4545 | VS |
| 0.4277 | VS |
| 0.3915 | VS |
| 0.3726 | VS |

[a] The powder X-ray diffraction pattern provided is based on a relative intensity scale in which the strongest line in the XRD pattern is assigned a value of 100: W = weak (>0 to ≤20); M = medium (>20 to ≤40); S = strong (>40 to ≤60); VS = very strong (>60 to ≤100).

It is known that certain lines in the XRD patterns of zeolites tend to broaden as the relevant dimension of the zeolite crystal decreases so that adjacent lines may begin to overlap and thereby appear as only partially resolved peaks or as unresolved broad peaks. FIG. 1 compares the powder XRD patterns of a conventional (standard) sample of SSZ-32 (top pattern) and SSZ-32x prepared according to the present disclosure (bottom pattern).

The powder X-ray diffraction patterns presented herein were collected by standard techniques. The radiation was $CuK_\alpha$ radiation. The peak heights and the positions, as a function of 2θ where θ is the Bragg angle, were read from the relative intensities of the peaks, and d, the interplanar spacing corresponding to the recorded lines, can be calculated.

Adsorption and Catalysis

The present zeolite may be useful as an adsorbent or as a catalyst in organic compound (e.g., hydrocarbon) conversion reactions where high activity is important. Examples of organic compound conversion processes which may be catalyzed by the present zeolite include isomerization and the conversion of organic oxygenates to hydrocarbons, such as gasoline boiling components, olefins and aromatics.

When combined with a hydrogenation component (e.g., Pt, Pd or Re), catalysts containing SSZ-32x produced by the present method can be useful in the isomerization dewaxing of paraffinic hydrocarbon feedstocks. Suitable paraffinic hydrocarbon feedstocks can range from relatively light distillate fractions such as kerosene and jet fuel up to high boiling stocks such as whole crude petroleum, reduced crudes, vacuum tower residua, cycle oils, synthetic crudes (e.g., shale oils, tars and oil, etc.), gas oils, vacuum gas oils, foots oils, Fischer-Tropsch derived waxes, and other heavy oils. Straight chain n-paraffins either alone or with only slightly branched chain paraffins having 16 or more carbon atoms are sometimes referred to as waxes. The feedstock will often be a $C_{10+}$ feedstock generally boiling above about 350° F. (177° C.) since lighter oils will usually be free of significant quantities of waxy components. However, the catalyst is particularly useful with waxy distillate stocks such as middle distillate stocks including gas oils, kerosenes, and jet fuels, lubricating oil stocks, heating oils and other distillate fractions whose pour point and viscosity need to be maintained within certain specification limits. Lubricating oil stocks will generally boil above 450° F. (230° C.), more usually above 600° F. (315° C.). Hydroprocessed stocks are a convenient source of stocks of this kind and also of other distillate fractions since they normally contain significant amounts of waxy n-paraffins. The feedstock will normally be a $C_{10+}$ feedstock containing paraffins, olefins, naphthenes, aromatic and heterocyclic compounds and with a substantial proportion of higher molecular weight n-paraffins and slightly branched paraffins which contribute to the waxy nature of the feedstock. During the processing, the n-paraffins are isomerized to branched paraffins but also undergo some cracking or hydrocracking to form liquid range materials which contribute to a low viscosity product. The degree of cracking which occurs is, however, limited so that the yield of products having boiling points below that of the feedstock is reduced, thereby preserving the economic value of the feedstock.

Process conditions for isomerization/dewaxing can include a temperature of from 392° F. to 800° F. (200° C. to 427° C.), e.g., from 482° F. to 752° F. (250° C. to 400° C.); a pressure of from 100 to 3000 psig (0.79 to 20.77 MPa), e.g., from 200 to 2500 psig (1.48 to 17.34 MPa); and a liquid hourly space velocity of from 0.1 to 10 $h^{-1}$, e.g., from 0.1 to 5 $h^{-1}$; and a hydrogen treat gas rate of from 250 to 10,000 scf/B (45 to 1780 $m^3/m^3$), e.g., from 500 to 5000 scf/B (89 to 890 $m^3/m^3$).

Catalysts containing SSZ-32x produced by the present method may be used for the conversion of organic oxygenates to hydrocarbons, such as gasoline boiling components, olefins and aromatics. Suitable organic oxygenates can include oxygenates containing at least one $C_1$-$C_4$ alkyl group (e.g., oxygenates containing at least one $C_1$-$C_3$ alkyl group). In some aspects, the oxygenates can include or be methanol and/or dimethyl ether. The oxygenate feed can be derived from any convenient source. For example, the oxygenate feed can be formed by reforming of hydrocarbons in a natural gas feed to form synthesis gas ($H_2$, CO, $CO_2$, etc.), and then using the synthesis gas to form alcohols.

Process conditions for converting organic oxygenate(s) to hydrocarbons can include a temperature of 150° C. to 600° C.; a total pressure of 0.1 to 500 psia (0.7 kPaa to 3.5 MPaa); and an oxygenate space velocity of 0.1 $h^{-1}$ to 20 $h^{-1}$, based on weight of oxygenate relative to weight of catalyst.

EXAMPLES

The following illustrative examples are intended to be non-limiting.

Example 1

1.08 g of CBV780 Y-zeolite powder (Zeolyst International, $SiO_2/Al_2O_3$ molar ratio=80), 0.90 g of dipropylamine ($CH_3CH_2CH_2NHCH_2CH_2CH_3$), 4.86 g of deionized water, and lastly, 0.36 g of concentrated HF were mixed together in a Teflon liner. The liner was then capped and placed within a Parr Steel autoclave reactor. The autoclave was placed in a rotating spit (43 rpm) in an oven and heated at 160° C. for 6 days. The solid products were recovered from the cooled reactor by filtration, washed with deionized water and dried at 95° C.

The resulting as-synthesized product was analyzed by powder XRD, scanning electron microscopy (SEM), and Energy Dispersive X-ray (EDX) analysis.

The powder XRD pattern presented in FIG. 1 is consistent with the product being a pure small crystal form of SSZ-32 (i.e., SSZ-32x).

Scanning Electron Microscopy (not shown) indicated that the product was composed of aggregates of small elongated crystals having a crystallite size in a range of 15 to 60 nm.

The as-synthesized product had a $SiO_2/Al_2O_3$ molar ratio of 66, as determined by EDX analysis.

Example 2

Example 1 was repeated with the exception that CBV780 Y-zeolite was replaced with HSZ®-390HUA USY-zeolite (Tosoh, $SiO_2/Al_2O_3$ molar ratio=500).

Powder XRD showed the product to be a pure small crystal form of SSZ-32 (i.e., SSZ-32x).

Example 3

A Teflon liner was charged with 3 g of a sol of aluminum coated onto silica (30% solids, $SiO_2/Al_2O_3$ molar ratio=130) and diluted out with 5.25 g of deionized water. Then carefully, dipropylamine (0.90 g) was added followed by 0.36 g of 50% HF. The liner was then capped and placed within a Parr Steel autoclave reactor. The autoclave was placed in a rotating spit (43 rpm) in an oven and heated at 160° C. for 6-12 days. The solid products were recovered from the cooled reactor by filtration, washed with deionized water and dried at 95° C.

Powder XRD showed the product to be a pure small crystal form of SSZ-32 (i.e., SSZ-32x).

Example 4

Material from Example 2 was calcined in air at 595° C. for 5 hours. After calcination, the material was loaded with platinum by mixing for three days at room temperature 4.5 g of a 0.148 N $NH_4OH$ solution with 5.5 g of deionized water and then a $(NH_3)_4Pt(NO_3)_2$ solution (buffered at pH 9.5) such that 1 g of this solution mixed in with 1 g of zeolite provided a 0.5 wt. % Pt loading. The recovered Pt/SSZ-32x zeolite was washed with deionized water, dried at 95° C., and then calcined to 300° C. for 3 hours. The calcined Pt/SSZ-32x catalyst was then pelletized, crushed, and sieved to 20-40 mesh.

Figure 2A:
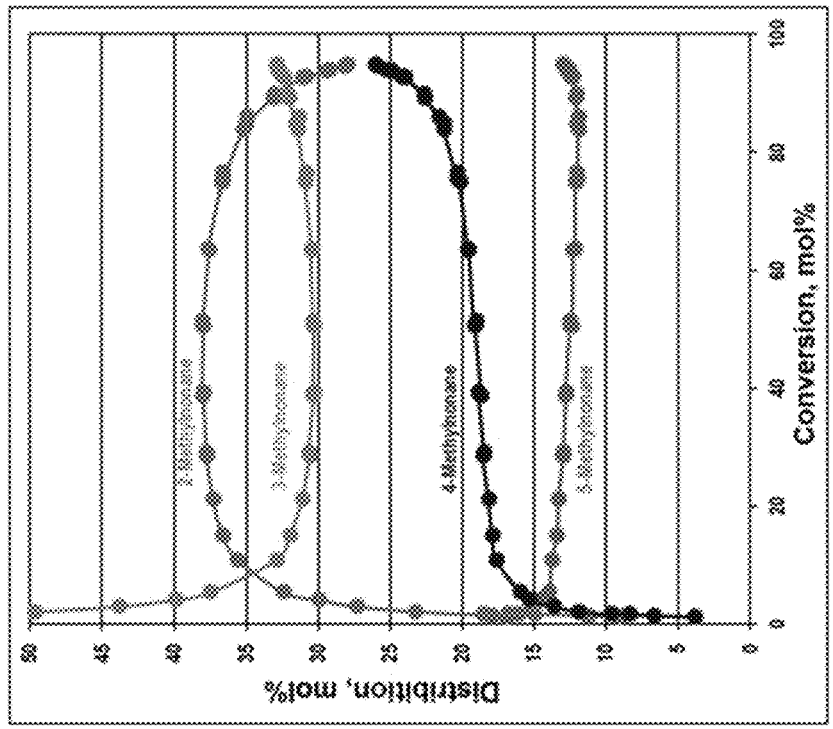
FIGS. 2(a) and 2(b) show the results of selective hydroconversion of n-decane over the Pt/SSZ-32x catalyst of Example 4.
Figure 2B:
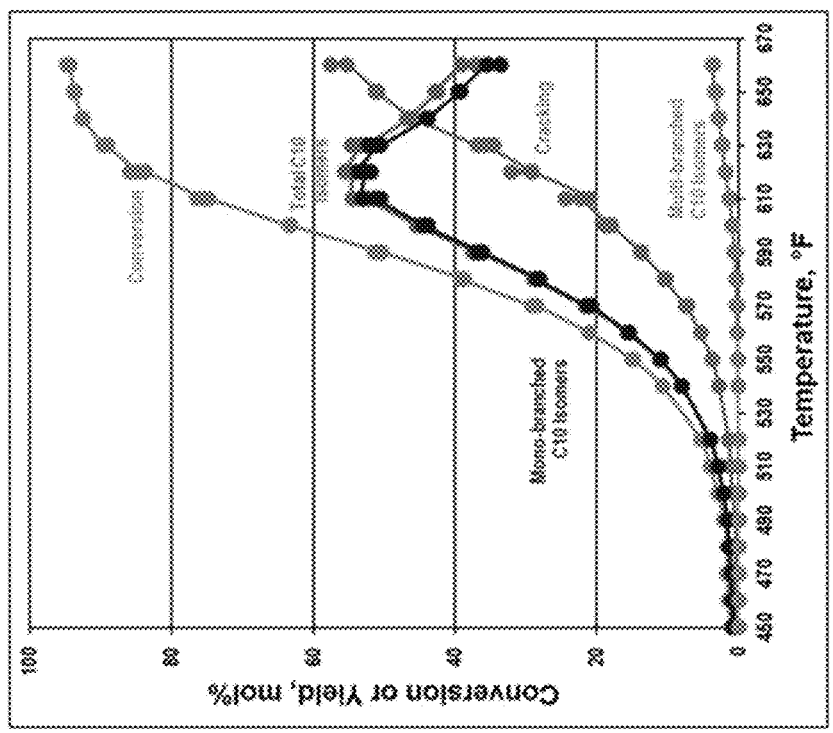

Hydroconversion of n-Decane 0.5 g of this Pt/SSZ-32x catalyst was loaded in the center of a 23 inch-long by 0.25 inch outside diameter stainless steel reactor tube with alundum loaded upstream of the catalyst for preheating the feed (a total pressure of 1200 psig; a down-flow hydrogen rate of 160 mL/min when measured at 1 atmosphere pressure and 25° C.; and a down-flow liquid feed rate of 1 mL/hour). All materials were first reduced in flowing hydrogen at about 315° C. for 1 hour. Products were analyzed by on-line capillary gas chromatography (GC) once every 60 minutes. Raw data from the GC was collected by an automated data collection/processing system and hydrocarbon conversions were calculated from the raw data. Conversion is defined as the amount n-decane reacted to produce other products (including iso-$C_{10}$). Yields are expressed as mole percent of products other than n-decane and include iso-$C_{10}$ isomers as a yield product. The results are shown in FIGS. 2(a) and 2(b).

Example 5

Figure 3B:
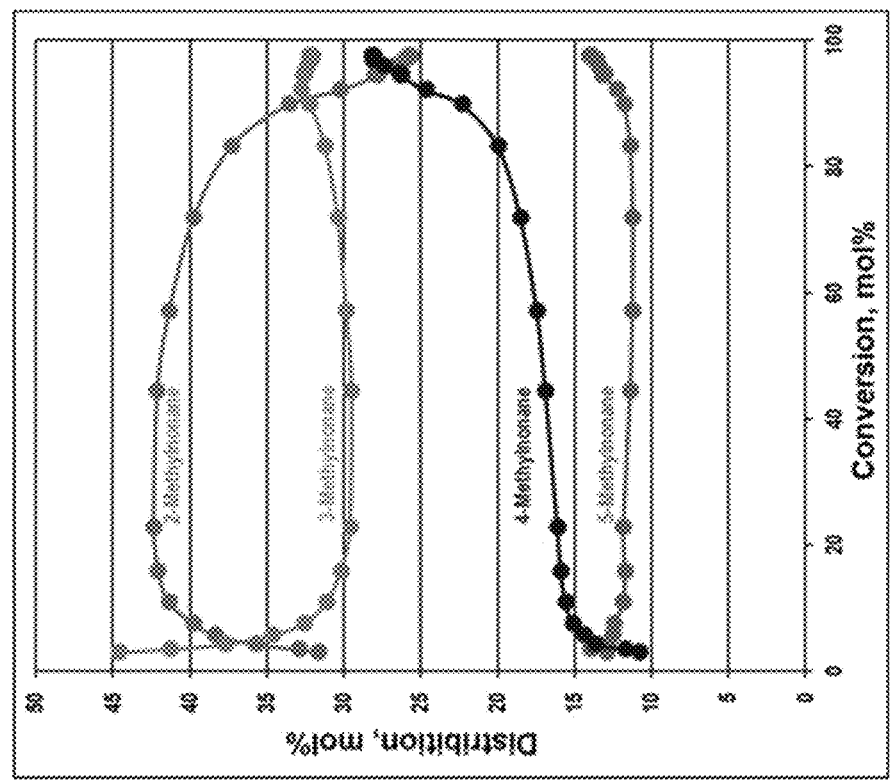
FIGS. 3(a) and 3(b) show the results of selective hydroconversion of n-decane over the Pt/SSZ-32x catalyst of Example 5.
Figure 3A:
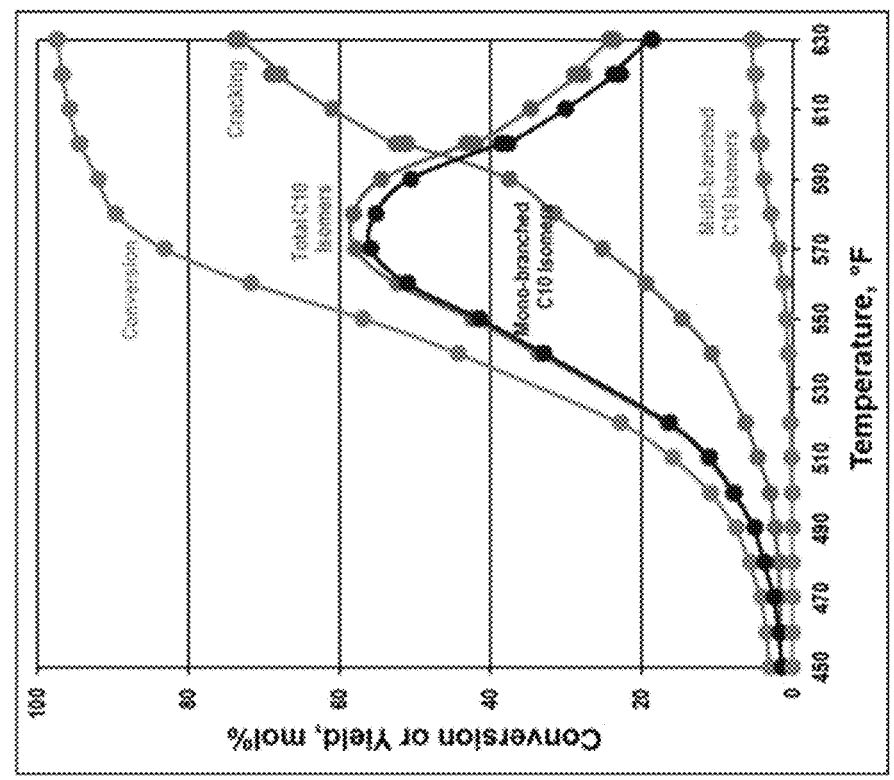

Platinum loading was carried out on the material from Example 3 per the teachings of Example 4. The platinum-loaded sample was tested for the selective hydroconversion of n-decane under the conditions described in Example 4. The results are presented in FIGS. 3(a) and 3(b).

The results show that the temperature of reaching maximum isomerization is lower for the catalyst of Example 5 than for the catalyst of Example 4. This is believed to be due to higher incorporation of aluminum in the catalyst of Example 5. Catalysts of Examples 4 and 5 both show that the products are substantially free of undesirable multi-branched $C_{10}$ isomers as SSZ-32x is a very narrow pore zeolite.

The invention claimed is:

1. A method of synthesizing zeolite SSZ-32x having a crystallite size of less than 100 nm, the method comprising:
   (a) preparing a reaction mixture comprising:
      (1) a source of silicon oxide;
      (2) a source of aluminum oxide;
      (3) dipropylamine (Q);
      (4) a source of fluoride ions; and
      (5) water; and
   (b) subjecting the reaction mixture to crystallization conditions sufficient to form crystals of the zeolite,
   wherein the source of silicon oxide and aluminum oxide is selected from the group consisting of a Y zeolite, a sol of aluminum coated onto silica, and combinations thereof.

2. The method of claim 1, wherein the reaction mixture has a composition, in terms of molar ratios, as follows:

| | |
|---|---|
| $SiO_2/Al_2O_3$ | ≥50 |
| $Q/SiO_2$ | 0.10 to 0.60 |
| $F/SiO_2$ | 0.10 to 0.60 |
| $H_2O/SiO_2$ | 10 to 60. |

3. The method of claim 1, wherein the reaction mixture has a composition, in terms of molar ratios, as follows:

| | |
|---|---|
| $SiO_2/Al_2O_3$ | 50 to 500 |
| $Q/SiO_2$ | 0.10 to 0.60 |
| $F/SiO_2$ | 0.10 to 0.60 |
| $H_2O/SiO_2$ | 15 to 40. |

4. The method of claim 1, wherein the crystallization conditions include a temperature of from 125° C. to 200° C.

5. The method of claim 1, wherein the SSZ-32x zeolite has a crystallite size in a range of 15 to 60 nm.

6. An SSZ-32x zeolite having a $SiO_2/Al_2O_3$ molar ratio of at least 50 and having a crystallite size of less than 100 nm.

7. The SSZ-32x zeolite of claim 6, wherein the $SiO_2/Al_2O_3$ molar ratio is from 50 to 500.

8. The SSZ-32x zeolite of claim 6, further comprising dipropylamine in its pores.

9. The SSZ-32x zeolite of claim 6, having a crystallite size in a range of 15 to 60 nm.

10. The SSZ-32x zeolite of claim 6, having an X-ray diffraction pattern the same as or consistent with that of SSZ-32x in FIG. 1.

11. A process for converting a feedstock comprising an organic compound to a conversion product which comprises contacting the feedstock at organic compound conversion conditions with a catalyst comprising an active form of the SSZ-32x zeolite of claim 6.

* * * * *